United States Patent [19]

Francis et al.

[11] Patent Number: 5,354,688

[45] Date of Patent: * Oct. 11, 1994

[54] ANAEROBIC MICROBIAL REMOBILIZATION OF COPRECIPITATED METALS

[75] Inventors: Arokiasamy J. Francis, Middle Island; Cleveland J. Dodge, Wading River, both of N.Y.

[73] Assignee: Associated Universities, Inc., Washington, D.C.

[ * ] Notice: The portion of the term of this patent subsequent to Sep. 10, 2008 has been disclaimed.

[21] Appl. No.: 869,397

[22] Filed: Apr. 16, 1992

Related U.S. Application Data

[63] Continuation-in-part of Ser. No. 522,036, May 11, 1990, abandoned.

[51] Int. Cl.$^5$ .............. C12P 3/00; C12N 1/20; A61L 9/01; B09B 3/00
[52] U.S. Cl. .................. 435/262; 435/168; 435/252.7; 435/266; 435/262.5; 210/611; 75/392; 423/1
[58] Field of Search .............. 435/262, 262.5, 842, 435/168, 252.7, 266; 210/611; 75/392, 393, 397, 399; 423/1, DIG. 17

[56] References Cited

U.S. PATENT DOCUMENTS

| | | | |
|---|---|---|---|
| 4,758,345 | 7/1988 | Francis et al. | 210/611 |
| 4,789,478 | 12/1988 | Revis et al. | 210/611 |
| 5,047,152 | 9/1991 | Francis et al. | 210/611 |

OTHER PUBLICATIONS

Leckie et al. "Absorption/Coprecipitation of Trace Elements" CS-1513 Research Report 910-1 Sep. 1980 S-1-S-3.
De Carlo et al. "Removal of Ansenic from Geothermal Fluids" *Environ. Sci. Technol.* vol. 19, No. 6, 1985 pp. 538-544.
Francis et al. "Anerobic Microbiol Dissolution of Transition and Heavy Metal Oxides" *Applied & Environmental Microb.* vol. 54, No. 4, pp. 1009-1014.

*Primary Examiner*—Michael G. Witshyn
*Assistant Examiner*—T. J. Reardon
*Attorney, Agent, or Firm*—Margaret C. Bogosian

[57] ABSTRACT

A process is provided for solubilizing coprecipitated metals. Metals in wastestreams are concentrated by treatment with an iron oxide coprecipitating agent. The coprecipitated metals are solubilized by contacting the coprecipitate with a bacterial culture of a Clostridium species ATCC 53464. The remobilized metals can then be recovered and recycled.

17 Claims, 4 Drawing Sheets

ANAEROBIC MICROBIAL REMOBILIZATION OF COPRECIPITATED METALS

This invention was made with government support under Contract Number DE-AC02-76CH00016 between the U.S. Department of Energy and Associated Universities, Inc. The Government has certain rights in the invention.

This application is a continuation-in-part of copending application Ser. No. 522,036 filed May 11, 1990, now abandoned.

BACKGROUND OF THE INVENTION

1. Field of the Invention

The invention relates to the separation of metal from a coprecipitate by contacting the coprecipitate with a Clostridium sp. ATCC No. 53464.

2. Description of the Related Art

Metals such as transition metals and heavy metals are present in soils, sediments and energy wastes. There is a significant input of metals into terrestrial and aquatic ecosystems from solid waste disposal and from atmospheric deposition of anthropogenic pollutants. Many of these metals are toxic, for example, arsenic, cadmium, cobalt, copper, mercury, nickel, lead, selenium, zinc and others.

A method for scavenging metals from power plant wastestreams using amorphous iron oxyhydroxide (Fe(OH)$_3$) has been described by J. O. Leckie, et al., Adsorption/Coprecipitation of Trace Elements From Water With Iron Oxyhydroxide, Electric Power Research Report CS-1513, Palo Alto, Calif., 1980. Naturally occurring oxides may act as sink for metals in the terrestrial and aquatic environments. A method using ferric iron from colloidal ferric hydroxide, FeCl$_2$ and Fe$_2$(SO$_4$)$_3$ as a coprecipitant and laurylammonium chloride as a collector has been described for coprecipitating arsenic from geothermal brine of high ionic strength ( E. H. DeCarlo and D. M. Thomas, Environ. Sci. Technol. 19, 538–544 (1985)).

U.S. Pat. No. 4,519,913 to Baldwin et al. and U.S. Pat. No. 4,519,912 to Kauffman et al. describe methods for removing certain ions from aqueous solutions by contacting the solutions with bacteria of the genus Clostridium to convert soluble ions to an insoluble form. Kauffman et al. utilize both a Clostridium and a Desulfovibrio or Desulfotomaculum. However, coprecipitation and subsequent solubilization of ions are not suggested.

U.S. Pat. No. 3,829,377 to Hashimoto et al. discloses using Clostridium bacteria in conjunction with a C$_{1-3}$ hydrocarbon to denitrify water. U.S. Pat. No. 4,510,243 to Haga et al. discloses the use of Clostridium bacteria for treating cellulose-containing water.

U.S. Patent Nos. 4,826,602, 4,789,478, 4,732,681, 4,728,427 and 4,522,723 describe processes for reducing ionic species in aqueous solutions using various bacterial microorganisms. None of these suggests coprecipitation followed by solubilization.

U.S. Pat. No. 4,758,345 to Francis et al. describes a method for the dissolution of lead oxide in industrial wastes through the action of acids produced by Clostridium sp. ATCC No. 53464. The disclosure is specifically directed toward solubilizing lead oxide through the production of organic acids and the lowering of the pH and no coprecipitation is suggested nor is the use of direct bacterial enzymatic action to solubilize a coprecipitate suggested.

It is therefore an object of the invention to provide a method for separating metals from a coprecipitate. It is a further object to remove metal from fluids by coprecipitating the metal and then separating the metal from the coprecipitate. It is another object of the invention to provide a method for microbial remobilization of metals coprecipitated with coprecipitating agents.

DEPOSIT

The bacterium utilized in the present invention is a nitrogen-fixing Clostridium sp. which has been deposited in the American Type Culture Collection (Rockville, Md. Feb. 20, 1986) in accordance with the Manual of Patent Examining Procedure MPEP §608.01(p)C and prior to the filing of this application. This deposit assures the permanence and availability to the public of the bacterium for at least the life of the patent. This Clostridium sp. has been accorded deposit number ATCC No. 53464.

SUMMARY OF THE INVENTION

A method is provided for separating or solubilizing metal from an iron oxide-metal coprecipitate by contacting the coprecipitate with a bacterial culture containing Clostridium sp. ATCC No. 53464 in a nutrient medium which satisfies the nutritional requirements of the bacterial culture.

Metal ions may be removed from fluids by precipitating the ions with an iron oxide coprecipitating agent thus forming a coprecipitate. The coprecipitate may thereafter be treated with a culture of the Clostridium species or its metabolites to solubilize the ions.

Advantageously, the metal ions may be solubilized from the coprecipitate through either the direct or indirect effects of the bacterial culture. In a direct manner, the bacteria effect enzymatic reductive dissolution of the coprecipitate. In an indirect manner, bacterial metabolites can contribute to effect the solubilization of coprecipitated metals, even in the absence of bacterial cells. Because of the different modes of solubilization, many different complexed metals may be solubilized using the invention regardless of the nature of the association of the metal with the coprecipitate.

Advantageously, economically important metals such as gold, silver, platinum and palladium can be salvaged from waste streams. Even more advantageously and of economic importance is the suitability of the invention for use in remobilizing toxic metals coprecipitated with iron oxides in wastes, contaminated soils and sediments.

For a better understanding of the present invention, together with other and further objects, reference is made to the following description, taken together with the accompanying drawings, and its scope will be pointed out in the appended claims.

DETAILED DESCRIPTION OF THE INVENTION

Figure 1:
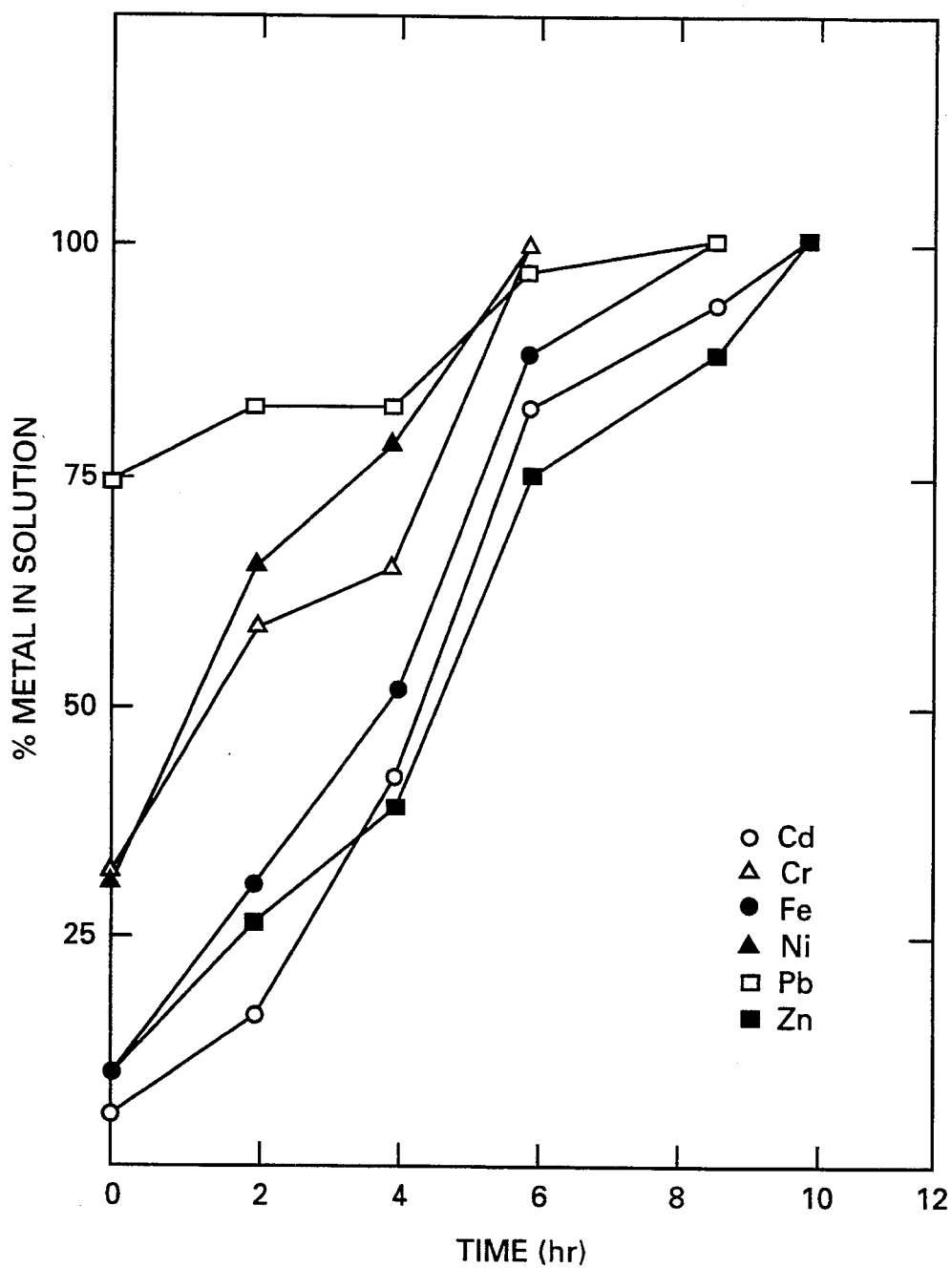
FIG. 1 is a graph illustrating dissolution profiles of coprecipitated mixed metals in acid.

Metal-containing solutions advantageously treated with the process of the invention include waste streams from industrial and manufacturing processes such as chemical, metal processing, mining and electroplating industries; also fossil- and nuclear-fuel cycle waste streams and geothermal fluids. In the case of dissolved metals in wastestreams, the stream may be first treated with a coprecipitating agent to coprecipitate the dissolved metal, and then the metal may be removed from the coprecipitate using a bacterium. Concentrations of dissolved metals in treated fluids may be as high as about 100,000 ppm, and streams containing from about 1 to about 10,000 ppm dissolved metals are preferably treated.

In some cases, naturally occurring coprecipitating agents such as iron oxides are already present in the environment, acting as a sink for metals and resulting in a natural production of a metal complex. In this case, the naturally occurring metal complex, which may be in the form of a coprecipitate, may be bacterially treated according to the invention to solubilize the complexed metal.

Dissolved metal can be separated from a fluid such as a wastestream by contacting the metal-containing fluid with a coprecipitating agent to form a coprecipitate. The metal may then be separated from the coprecipitate by contacting the coprecipitate with a bacterial culture of Clostridium sp. ATCC No. 53464. This contacting causes the metal to solubilize and the metal can then be removed from solution by chemical separation using known methods.

Elements which may be separated from a stream or a coprecipitate using this process include alkali metals, alkaline-earth metals, transition metals, heavy metals, rare earth metals, metals of the Lanthanide and Actinide series and transuranic metals. This includes elements in the Groups IA, IIA, IIIA, IVA, VA, VIA, IB, IIB, IIIB, IVB, VB, VIB, VIIB, VIII and the Lanthanide and Actinide Series of the Periodic Table of the Elements, CAS version..

Representative metals include, for example, Transition Metals: Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Gold, Cadmium, Halfnium, Tantalum, Tungsten, Rhenium, Osmium, Iridium, Platinum, Silver, Mercury, Actinides: Thorium, Protactinium, Uranium, Neptunium, Plutonium, Americium, Curium, Berkelium, Californium, Einsteinium, Mendelevium, Nobelium, and Lawrencium, including the transuranic elements which are elements having a higher atomic number than Uranium.

The method of the invention is particularly advantageous in removing transition metals, actinides and transuranic elements. Even more preferably treated are, for example, streams or coprecipitates containing Cd, Co, Cr, Cu, Mn, Ni, Pb, Zn, Au, Ag, Pt and Pd.

The invention has been shown to be particularly useful in removing Cd, Cr, Ni, Pb and Zn.

When coprecipitates of certain metals such as some Actinides, in particular uranium and thorium, are bacterially treated, their removal from the coprecipitate is by solubilization followed by biosorption, i.e., incorporation into biomass, and precipitation. In any case, by coprecipitation the metals are removed from wastestreams and by subsequent contacting with bacteria, the metals are solubilized and can be recovered and recycled.

A wide variety of compounds may be used as coprecipitating agents. By coprecipitation is meant that soluble metals within a solution phase accompany a coprecipitating agent in forming a solid phase, and thereby the soluble metal is removed from solution.

A coprecipitating agent is intended to mean a chemical compound which is capable of complexing with metals in solution thereby forming a solid phase or coprecipitate which includes the coprecipitating agent and the metal. Coprecipitating agents suitable for use in the invention include compounds capable of scavenging or trapping metal and later releasing the metal through a reduction or dissolution process. Suitable compounds are, for example, iron oxides, but the invention is not limited to these.

The iron oxides include magnetite ($Fe_3O_4$, ferrous-ferric oxide), hematite ($Fe_2O_3$, iron (III) oxide), limonite ($2Fe_2O_3 \cdot H_2O$, hydrous or brown amorphous iron oxide), and goethite ($HFeO_2$).

Other suitable iron oxides are the ferrites. Some metal ions may associate with iron oxides to form a complex oxide called a ferrite. Ferrites are mixed-valence iron oxide compounds having the general formula $XY_2O_4$, with a crystal structure related to spinel, $MgAl_2O_4$. They exist in an inverse or normal structure, depending upon the preference of the individual ions for octahedral coordination with oxygen. In the normal spinel, the iron is present solely in the octahedral coordination, with the divalent metal in the tetrahedral coordination. In the inverse spinel, the iron is present in both octahedral and tetrahedral coordinations, and the divalent metal is present only in octahedral coordination with iron. The formation of ferrites occurs, for example, when metals such as Cd, Co, Ni, Mn and Zn are contacted with an aqueous suspension of lepidocrite ($\gamma$-FeOOH). The spinel structure of ferrites may have the general formula $MFe_24$, where M is a divalent metal ion. In the unit cell of this structure there are 8 tetrahedral and 16 octahedral sites for the cations. The cations in the tetrahedral and octahedral sites are surrounded by four and six oxygen ions, respectively. Cadmium and zinc form tetrahedral associations in normal ferrites, while nickel and lead form octahedral coordination with Fe as inverse spinels. The tetrahedral normal ferrites are more stable than Ni and Pb ferrites. Typically the ferrites are bimetallic and have a crystal structure which has more than one site for cations. Representative ferrites are, for example, $CuFe_2O_4$, $MnFe_2O_4$, $CoFe_2O_4$, and $ZnFe_2O_4$.

Of the iron oxides, preferred as coprecipitating agents are goethite and the ferrites.

The solubility of the coprecipitating agent is an important factor because scavenged metals can be separated from the coprecipitate through dissolution of the coprecipitate. The nature of the coprecipitating agent affects the solubility of the coprecipitate. As an example, iron oxides are suitable as coprecipitating agents. In general, the solubility of iron oxides depends upon the degree of crystallinity. Amorphous iron oxides are orders of magnitude more soluble than goethite or hematite (Jenne, F. A., *Molybdenum in the Environment*; Chappel et al. Eds., Marcel Dekker, Inc., New York 1977, Vol. 2, pp. 425–553), while amorphous synthetic goethite is 2–100 times more soluble than a well-crystallized geothite (Berner, R. A., Geochim. Cosmochim. Acta 33, 267–273 (1969)).

After the fluid or wastestream has been treated to remove metal ions through the formation of a coprecipitate, the coprecipitate is treated to cause solubilization of the metal. The microorganisms of the invention can play a role in the dissolution of amorphous and crystalline forms of iron oxides by direct action and release of metals associated with iron by indirect action. Direct action involves enzymatic reductive dissolution of iron from a higher oxidation state to a lower oxidation state. Indirect action can be caused by microbial metabolites, as well as by lowering the pH. These direct and indirect actions caused by microorganisms can result in dissolution of coprecipitates with a concurrent solubilization of metals.

Sorption and coprecipitation are the predominant processes by which most of the metals are retained by iron oxide or other coprecipitating agents. Coprecipitation is the simultaneous precipitation of a chemical element with other elements and includes mixed-solid formation, adsorption and inclusion (G. Sposito, in *Applied Environmental Geochemistry*, Thornton, I., Ed., Academic Press, New York, 1988, pp. 123–170). Although coprecipitation has not been as well studied as adsorption, coprecipitation appears to remove trace metals from solution more efficiently than adsorption.

The extent of microbial remobilization of coprecipitated metals depends, in part, on the nature of the association of the metals with the coprecipitating agent. Metals that are closely associated, that is, chemically bound, with the metal in the precipitating agent are solubilized along with the metal of the precipitating agent by direct action, i.e. direct enzymatic reduction. Metals may also be more loosely bound in a complex. These can be expected to be removed more easily than closely associated metals by indirect chemical action.

When a coprecipitating agent is to coprecipitate dissolved metal in a fluid, contacting of the coprecipitating agent and the metal-containing fluid or wastestream may be at a temperature of from about 0° C. to about 110° C., preferably from about 15° to about 80° C. and most preferably from about 20° to about 60° C.; at a pH of 7.5–14, preferably a pH of 8–13 and most preferably a pH of 9–12.5. The treated fluid effluent is characterized by a significantly lower concentration of water soluble ionic metal.

The coprecipitating agent may be formed by chemical reaction in situ, or may be pre-synthesized and added to the metal-containing fluid. In coprecipitating dissolved metal, the ratio of mole percent of coprecipitating agent to mole percent of dissolved metal present in the treated fluid will vary according to the coprecipitating agent used and the metals to be coprecipitated. One skilled in the art can determine optimum ratios with routine experimentation. However, an excess of coprecipitating agent is preferred for thorough removal of the metals from the fluid. The ratio may therefore be at least about 1:1, with 10:1 preferred, and 100:1 more preferred.

The coprecipitate formed may be removed from the fluid by filtration or other known means. For bacterial treatment, the coprecipitate may subsequently be suspended in an appropriate medium such as growth medium, or mixed directly with bacterial medium in a fluidized process in order to solubilize the coprecipitated metal.

Bacterial contacting may be in a batch process or in a continuous process. Either process may be carried out in any suitable enclosure. A continuous process may be carried out such that treated fluid is periodically removed while coprecipitate and fresh nutrient medium are periodically added.

In another embodiment, the fluid containing coprecipitate may be contacted with bacterial culture in a fixed bed process in which the bacteria is grown on a porous support such as glass or plastic beads, glass wool or sand and the coprecipitate-containing fluid is passed through and/or around the bed in an appropriate rate of flow, at appropriate temperature and time.

The coprecipitate is contacted with the bacterial culture under conditions sufficient to sustain the viability of the bacteria. Contacting is preferably under anaerobic conditions, that is, in the substantial absence of oxygen, most preferably under nitrogen gas, and under conditions to achieve a steady state population density. Population density varies from about $2 \times 10^6$ to $2 \times 10^9$ cells/mL of solution and is preferably about $2 \times 10^7$ to $2 \times 10^8$ cells/mL of solution. Contacting is at a temperature of from about 15° C. to about 37° C., preferably from about 18° C. to about 32° C., and most preferably from about 20° C. to about 30° C. The initial pH is preferably 5–8, most preferably 6–7.5. The coprecipitate solubilizes upon contact with the bacterial solution. Therefore contacting time can be as little as seconds under optimal conditions. In a batch system, contacting can be carried out for up to 48 hrs. Final pH after contacting and incubation may range from about 4.5–7.0 preferably 5.5–6.5.

The conditions for contacting are sufficient to cause a enzymatic reduction of the coprecipitate so that the metal is released.

EXAMPLE 1

Characterization and Growth of Clostridium sp. ATCC No. 53464

A nitrogen-fixing Clostridium sp. (ATCC 53464) isolated from coal-cleaning residue was grown in a medium containing the following: glucose, 5.0 g; $NH_4Cl$, 0.5 g; glycerol phosphate, 0.3 g; $MgSO_4.7H_2O$, 0.2 g; $FeSO_4.7H_2O$, 2.8 mg; $CaCl_2.2H_2O$, 0.5 g; peptone, 0.1 g; yeast extract, 0.1 g; deionized water, 1000 mL; pH, 6.8±0.1. The medium was first reduced by boiling and purging with $N_2$ gas for 15 min to remove the dissolved oxygen. It was then cooled under a $N_2$ atmosphere in an anaerobic glovebox and 40-mL quantities were dispensed in 60-mL serum bottles. The serum bottles were closed with butyl rubber stoppers, sealed with aluminum caps, and autoclaved. The medium was inoculated with 0.2 mL of an early logarithmic growth phase of the culture (optical density at 600 nm, 0.41) and incubated at 24°±1° C. Growth of the bacteria was measured at 600 nm with a Bausch and Lomb Spectronic-20 spectrophotometer.

EXAMPLE 2

Mixed Metal Goethite Coprecipitate

Stock solutions were prepared containing 0.25M of each of the following metals in 100 mL of deionized water: $Cd(NO_3)_2.4H_2O$ (Alfa Products, 95+%); $Cr(NO_3)_3.9H_2O$ (Alfa Products, 98.5%); $Ni(NO_3)_2.H_2O$ (Alfa Products, 97+%); $Pb(NO_3)_2$ (Mallinckrodt, analytical reagent grade); $Zn(NO_3)_2.xH_2O$ (Alfa Products, 95+%).

Each of the five stock solutions was acidified with 0.05 mL of Ultrex nitric acid and 5 mL of each was added to a 1.5-L Pyrex flask.

In order to coprecipitate the metals of the stock solutions, iron oxide coprecipitating agent was synthesized in situ according to the method of Atkinson, et al. J. Phys. Chem. 71, 550-558 (1967) with some modifications. $Fe(NO_3)_3 \cdot 9H_2O$ (Mallinckrodt, 98.5%) in an amount of 50 g and 800 mL of deionized water were added to the acidified mixture of stock solutions and the pH was adjusted to 12 by adding 200 mL of 2.5N KOH. A reddish brown goethite coprecipitate (hereinafter "precipitate") formed immediately. The precipitate suspension was aged for 24 hours at 60° C., the precipitate was separated from solution by centrifugation and then washed several times with deionized water until the nitrate levels in the supernatant were less than 5 mg/L. The washed precipitate was dried in an oven at 60° C. for 18 hours, pulverized to a fine powder in an agate mortar and stored in a dessicator. The structure of the iron oxide was confirmed by X-ray diffraction with a Phillips XRG 3100 Model analyzer.

EXAMPLE 3

Unmixed Metal Goethite Coprecipitate

A precipitate was prepared according to the procedure described in Example 2 except that the stock solution of $Pb(NO_3)_2$ was coprecipitated without the presence of the other four metals.

EXAMPLE 4

Total Metal Content 50-mg aliquots of each of the precipitates formed in Examples 2 and 3 were separately dissolved in 40 mL of 50% HCl in duplicate. The resulting solutions were filtered through a 0.22 μm Millipore filter, and the metal content of each precipitate was analyzed by atomic absorption spectrophotometry. The results are shown in Table I.

TABLE I

| | Metal Content of Goethite Coprecipitate | | |
|---|---|---|---|
| Ex. | metal | mmol/added | mmol in coprecip[a] | % metal incorp |
| | Mixed Metals | | | |
| 2 | Fe | 125 | 98.0 ± 0.00 | 78.4 |
| | Cd | 1.25 | 0.62 ± 0.01 | 50.0 |
| | Cr | 1.25 | 0.83 ± 0.00 | 66.6 |
| | Ni | 1.25 | 0.62 ± 0.01 | 50.0 |
| | Pb | 1.25 | 0.67 ± 0.01 | 53.8 |
| | Zn | 1.25 | 0.86 ± 0.06 | 69.2 |
| | Lead Only | | | |
| 3 | Fe | 125 | 100 ± 2 | 80.0 |
| | Pb | 1.25 | 0.77 ± 0.02 | 61.5 |

[a] ±1 standard error of the mean.

Analysis of the precipitates showed that they contained 78-80% of added iron. There were differences in the extent of the incorporation of different metals into the precipitate of goethite. About 69% of added Zn, 67% Cr, 54% Pb, and 50% each of Cd and Ni were found in the coprecipitate. More Pb was present in the lead-goethite co-precipitate than in the mixed metal coprecipitate.

EXAMPLE 5

Cation-Exchange Capacity

To determine the exchangeable fraction of metals in each precipitate, 40 mL of a 1M $MgCl_2$ solution was added to 50 mg of the precipitates of Examples 2 and 3 in duplicate. The solutions were shaken continuously for 2 hours on a wrist-action shaker. The samples were then filtered through a 0.22-μm Millex filter, acidified with 0.20 mL of Ultrex $HNO_3$, and analyzed for each metal. The results are shown in Table II.

TABLE II

| | Exchangeable Cations in Goethite Coprecipitate | | |
|---|---|---|---|
| Ex. | metal | mmol/g of dry wt | % |
| | Mixed Metals | | |
| 2 | Fe | <0.001 | <0.01 |
| | Cd | 0.002 | 2.9 |
| | Cr | <0.002 | <2.5 |
| | Ni | <0.002 | <2.5 |
| | Pb | 0.008 | 11.4 |
| | Zn | 0.001 | 1.1 |
| | Lead Only | | |
| 3 | Fe | <0.001 | <0.01 |
| | Pb | 0.011 | 13.8 |

In Table II, the exchangeable fraction of the metals in the coprecipitates is presented. Only small amounts of Cd and Zn were present in the exchangeable fraction; Fe, Cr and Ni were not detected. A substantial amount of Pb (11%) in the mixed-metal coprecipitate and about 14% in the lead-geothite coprecipitate were present in the exchangeable fraction. Exchangeable fraction of the metals are those that are replaced by the chloride solution. The exchangeable fraction represents metals that are more loosely bound as opposed to metals which are more closely associated.

EXAMPLE 6

Dissolution Profile of the Metals

To determine the dissolution profile of the metals, a 40 mL aliquot of 50% HCl was added to 50 mg of the precipitates of Examples 2 and 3 in duplicate. Six sets of duplicate samples were incubated and each was mixed by agitation at periodic intervals. At 0, 2, 4, 6, 8 and 10 hours a set of samples was filtered through a 0.22 μm Millex filter and analyzed for each metal.

FIG. 1 shows the dissolution profiles of the metals from the precipitates. The dissolution pattern of each metal was different and indicated the nature of the metal association in the precipitate. About 75% of Pb, 30% each of Cr and Ni, and less than 10% each of Fe, Cd and Zn were dissolved from the precipitate immediately upon the addition of the acid. Pb was solubilized most readily. Ni and Cr were solubilized at similar rates. The dissolution rates of Fe, Cd, and Zn were similar but greater than Ni and Cr. In addition, the slopes of percent metal versus iron released were calculated to be: Cd (1.01), Zn (1.00), Ni (0.84), Cr (0.83), and Pb (0.27). These data indicate that Cd and Zn are more closely associated with iron than Ni and Cr, and Pb is loosely associated with iron.

EXAMPLES 7-11

Dissolution of Metals from Goethite Coprecipitate 50 mg samples of the precipitates of Examples 2 and 3 were treated according to Examples 7-11 below and then incubated in 40 mL of sterile growth medium in 60-mL serum bottles fitted with butyl stoppers under nitrogen atmosphere for 40 hours at 24° C. For each treatment, the samples were incubated in triplicate. At the end of the treatments in Examples 7-11, the samples were filtered through a 0.22 μm Millex filter, the filtrate was acidified with Ultrex $HNO_3$ and analyzed for Fe, Cd, Cr, Ni, Pb and Zn by atomic absorption spectrophotometry. Organic acid metabolites were determined by High Pressure Liquid Chromatography. All manipulations were performed under anaerobic conditions. The treatments consisted of the following:

EXAMPLE 7

Dissolution in Sterile Medium (Control)

Figure 2:
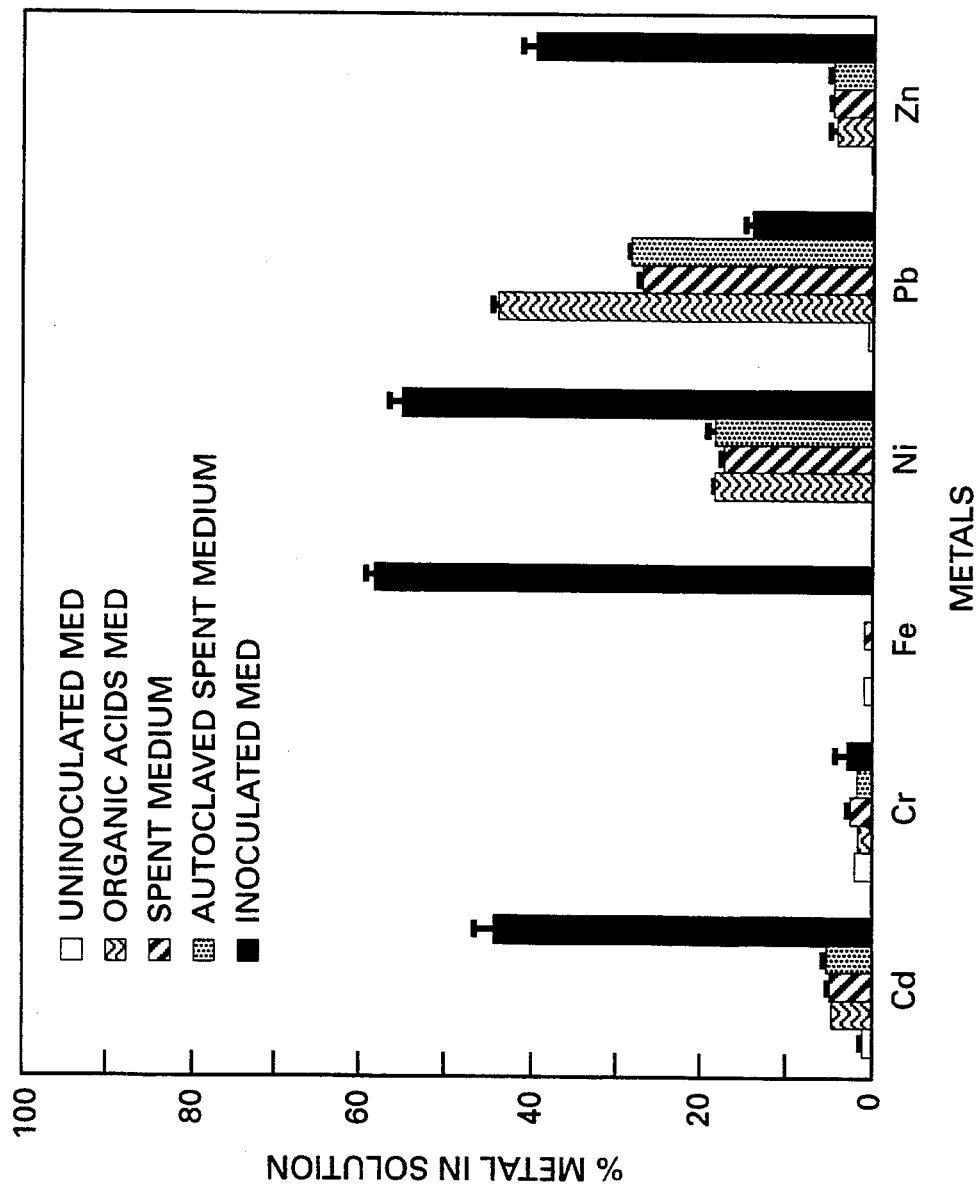
FIG. 2 is a graph comparing the dissolution of coprecipitated mixed metals under various conditions.

To determine the chemical dissolution of each precipitate in the uninoculated bacterial growth medium (control), we added the medium, which had been prereduced as described in Example 1, to acid-washed bottles containing a prepared sample of the precipitates as described above. The samples were sealed with butyl rubber stoppers, autoclaved, and incubated for 40 hours. The results are shown in FIG. 2.

Dissolution of metals from the coprecipitate by uninoculated control medium (pH 6.7) was very low for Fe (1.1%), Cd (1.0%), and Zn (0.3%), while Cr, Ni, and Pb could not be detected. This finding indicates that there was little chemical dissolution caused by uninoculated culture medium alone.

EXAMPLE 8

Dissolution in the Presence of Bacteria

The serum bottles individually containing 40 mL of autoclaved medium and 50 mg of precipitates of Examples 2 and 3 or no precipitate (control) were inoculated with 0.2 mL of a 24-hour-old culture of Clostridium sp. ATCC No. 53464 and incubated. This treatment allowed the bacterial cells to come in direct contact with the coprecipitate. At the end of incubation, the total gas production and pH were determined. The results are shown in Table III.

TABLE III

| | Growth of Clostridium sp. in the Presence and Absence of Goethite Coprecipitate | | | |
|---|---|---|---|---|
| sample | goethite coprecip | final pH | total gas produced, mL | turbidity (600 nm) |
| | Mixed Metals | | | |
| uninoculated (control) | + | 6.70 | 0 | 0 |
| inoculated | − | 3.05 | 24 | 0.62 |
| inoculated | + | 4.33 | 50 ± 15* | ND** |
| | Lead Only | | | |
| inoculated | + | 4.35 | 52 ± 5 | ND |

*±1 standard error of the mean.
**ND, not determined because of high background turbidity caused by the coprecipitate.

The optical density (OD) of the culture medium without coprecipitate reached 0.62 after 40 hours of incubation and the pH changed from 6.8 to 3.1. Because of the high background turbidity caused by the presence of coprecipitate, the optical density of those culture samples could not be measured. However, as shown in Table III, the growth of bacterium was enhanced in samples containing the coprecipitate as evidenced by increased production of gas and changes in the pH of the culture medium during incubation from 6.7 to 4.3. The change in pH of the culture medium was due to production of acetic, butyric, and lactic acids from glucose fermentation. The higher pH of the culture medium containing the coprecipitate was probably due to the consumption of protons during the dissolution of the precipitating agent (goethite) or to release of hydroxide from the coprecipitate. The increased growth of the bacteria accompanied by higher gas production was probably due to this higher pH of the medium.

EXAMPLE 9

Dissolution by Filtered Cell-Free Spent Medium

To determine whether metals were released from the coprecipitate by extracellular components produced by the bacterium, a cell-free spent medium was prepared. Bacterial cells were grown in culture medium in the absence of coprecipitate. After 40 h of incubation (optical density at 600 nm, 0.61), the cells were separated from the culture medium by centrifugation at 13600g for 30 min and anaerobic filtration through a 0.22-μm Durapore filter in a 1.5-L Teflon-coated pressure filtration device (Millipore Co.). The spent medium was divided into two equal aliquots. The first aliquot was tested for its ability to solubilize metals from the coprecipitate according to the procedure described in Example 7 (50 mg of coprecipitate in 40 mL of spent medium). The results are shown in FIG. 2.

EXAMPLE 10

Nonenzymatic Dissolution of Metals By Heat-Inactivated Spent Medium

The second aliquot of filtered spent medium prepared in Example 9 was transferred to serum bottles, sealed with butyl rubber stoppers, and autoclaved to inactivate the enzymes. This heat-treated spent medium was filtered again through the pressure filtration device with a 0.22-μm Durapore filter to remove any denatured cellular material. The pH of the autoclaved and filtered spent medium was measured, and the dissolution of metals from the coprecipitate was determined as described above.

The filtered spent medium of Example 9 and the heat-treated spent medium of Example 10 were checked for cells by direct microscopic examination and for viable cells by incubating an aliquot in a fresh growth medium.

The results are shown in FIG. 2.

EXAMPLE 11

Dissolution of Metals by Synthetic Medium

To determine the effect of acid metabolites and pH of the medium on the dissolution of metals from the coprecipitates, a synthetic medium was prepared by adding metabolic acids to prereduced growth medium (40 mL) containing only inorganic salts ($NH_4Cl$, 0.50 g; $MgSO_4.7H_2O$, 0.20 g; and $CaCl_2.2H_2O$, 0.5 g/L). The metabolic acids, acetic (3.44 mM), butyric (7.90 mM), and lactic (2.62 mM), were added in the same proportions as found in an inoculated culture medium of Clostridium sp. The final pH of the synthetic medium was 3.1. 50 mg of the coprecipitates as prepared in Examples 2 and 3 were incubated with the synthetic medium.

At the end of incubation, the samples were filtered through a 0.22-μm Millex filter and the filtrate was acidified with Ultrex $HNO_3$ and analyzed for Fe, Cd, Cr, Ni, Pb, and Zn by atomic absorption spectrophotometry. All manipulations, except weighing the coprecipitate, were performed in the anaerobic glovebox.

The results are shown in FIG. 2.

Synthetic medium (pH 3.1) that contained the major metabolic acids (acetic, butyric, and lactic; plus mineral salts) solubilized substantial portions of Pb (44%), Ni (19%), and about 5% each of Cd and Zn. Only 0.04% of Fe was released and Cr was not detected.

Dissolution of Metals from Goethite Coprecipitate. FIG. 2 shows the extent of metals solubilized from the mixed-metal coprecipitate by (i) uninoculated sterile medium (control) (Example 7) which is represented by a blank bar on the graph, (ii) in the presence of bacteria (inoculated medium) which is represented by the solidly shaded bar on the graph (Example 8), (iii) cell-free spent medium which is represented by the diagonally solid striped bar (Example 9), (iv) autoclaved cell-free spent medium (nonenzymatic dissolution) which is represented by the herringbone pattern bar (Example 10), and (v) synthetic medium which is represented by the dotted bar on the graph (Example 11).

Cell-free spent medium (pH 3.1) containing microbial metabolites and extracellular enzymes dissolved the metals to varying degrees. More Fe was released than in the synthetic medium but the amount was similar to that in uninoculated control medium (1.1%). Similar amounts of Cd were solubilized in spent medium (5.1%) and in synthetic medium (4.8%). There were detectable amounts of soluble Cr (2.7%) in spent medium but not in uninoculated and synthetic medium, indicating that Cr dissolution was biochemically mediated. About 17.5% of Ni and 5.5% of Zn were solubilized from the coprecipitate by the cell-free spent medium, similar to their values in synthetic medium. Dissolution of Pb in the cell-free spent medium was about 15% less than that of the synthetic medium.

There was little difference in the extent of dissolution of Cd, Ni, and Zn in the spent medium, the autoclaved spent medium, and the synthetic medium, indicating that their dissolution is primarily due to the organic acid metabolites and low pH. Dissolution of Pb in the cell-free and autoclaved cell-free spent medium was similar but less than that in the synthetic medium. The soluble Fe and Cr in the autoclaved spent medium was much less than that of the spent medium. This finding indicates that heat-labile components present in the spent medium are involved in the solubilization of Fe and Cr.

A substantial increase in the concentrations of soluble Fe (59%), Cd (48%), Ni (55%), and Zn (41%) and a slight increase of Cr (3.2) was observed in samples incubated with cells. However, soluble Pb in the inoculated culture medium was 50% less than that of spent medium and 70% less than in the synthetic medium. This difference was due to biosorption by the cellular components in the medium. Analysis of Fe in solution showed that it occurred as $Fe^{2+}$. The data clearly show that the coprecipitated metals were released into the medium when iron was solubilized only in the presence of bacteria. These results also indicate that direct contact between the coprecipitate and the bacteria was required to effect remobilization of metals associated with iron.

Figure 3:
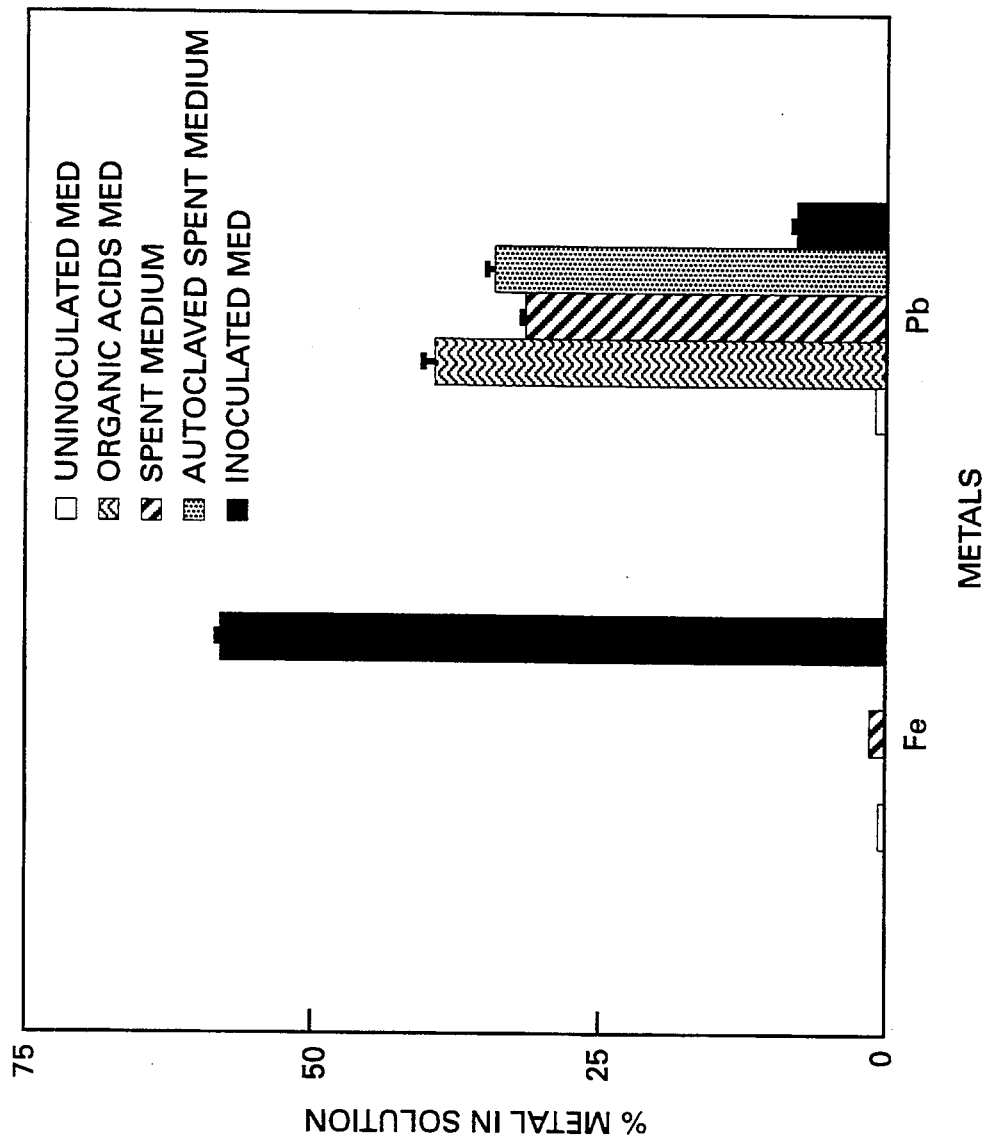
FIG. 3 is a graph illustrating the dissolution of coprecipitated unmixed metal.

The extent of lead and iron dissolution from the lead-goethite coprecipitate was similar to that of the mixed-metals-goethite coprecipitate (FIG. 3). Therefore, the association of Pb with coprecipitate appears to be unaffected by the presence of other cations that may compete with Pb for active sites. Dissolution of Pb from the coprecipitate was primarily due to organic acid metabolites. Soluble Pb detected in cell-free spent medium and autoclaved spent medium was much less than that of the synthetic medium. This was due to immobilization of soluble Pb by the extracellular materials present in the cell-free and autoclaved spent medium. In the presence of bacteria, however, soluble Pb detected in culture medium containing Pb-goethite coprecipitate was much less than that of culture medium containing mixed-metals-goethite coprecipitate. This may be due to the presence of other cations released from mixed-metals-goethite coprecipitate, which could compete for metal binding sites in the biomass.

EXAMPLE 12

Ferrite Coprecipitates

Ferrite precipitates of Co, Cu, Mn and Ni were simulated using prepared ferrites. Cobalt ferrite, $CoFe_2O_4$ (powder); copper ferrite $CuFe_2O_4$ (99% purity, −325 mesh); manganese ferrite, $MnFe_2O_4$ (99% purity, −325 mesh); nickel ferrite, $NiFe_2O_4$ (99.97% purity, electronic grade); and zinc ferrite, $ZnFe_2O_4$ (99% purity, −325 mesh) were obtained from Alfa Products, Danvers, Mass. The ferrites were washed in several changes of deionized water, dried at 60° C. overnight, and stored in a dessicator.

Composition of Ferrites. 1150 μg (4.8 μmoles) of each ferrite sample was weighed into 60 ml acid washed serum bottles in quadruplicate. Forty ml of Ultrex HCl (50%) was added to dissolve the ferrite and the metals were analyzed by atomic absorption spectrophotometry. Blanks (controls) without ferrite were also analyzed for background values. Table IV presents the total iron and the metal contents of each ferrite.

TABLE IV

| | Composition of Ferrites | | | |
|---|---|---|---|---|
| Ferrite | Spinel type | Iron (μmoles) | Metal (μmoles) | Ratio Fe/$M^{2+}$* |
| $CoFe_2O_4$ | Inverse | 8.88 ± 0.08** | 4.84 ± 0.12 | 1.83 ± 0.03 |
| $CuFe_2O_4$ | Inverse | 8.68 ± 0.14 | 3.98 ± 0.12 | 2.18 ± 0.04 |
| $MnFe_2O_4$ | Normal | 9.66 ± 0.10 | 4.14 ± 0.14 | 2.33 ± 0.05 |
| $ZnFe_2O_4$ | Normal | 8.58 ± 0.14 | 4.64 ± 0.08 | 1.85 ± 0.02 |

*$M^{2+}$ - divalent metal
**±1 standard error of the mean (1SEM)

These results show that the iron and the metal in the ferrites were not present in stoichiometric amounts as indicated by their structural formulas. Copper and manganese ferrites contained more iron than cobalt and zinc ferrites. Nickel ferrite was not soluble in 50% HCl. Therefore, the Ni and Fe contents of the nickel ferrite were not determined.

Examples 13–16

To determine the mechanism of dissolution of ferrites, 1150 μg (4.8 μmoles) of each ferrite was added to acid washed 60 ml serum bottles and treated as described below in Examples 13–16. Triplicate samples of each ferrite were incubated under anaerobic conditions for three days at 24°±1° C., unless otherwise stated. All samples were prepared in an atmosphere of $N_2$ in the anaerobic glove box.

Example 13

Dissolution of Ferrites

To determine the growth characteristics of the bacterium in the presence of ferrites and the dissolution of ferrites in the presence of the Clostridium sp. resulting from direct contact between the cells and the ferrite as well as by extracellular enzymes and/or metabolic products, 40 mL of prereduced bacterial growth medium as described in Example 1 but without the iron was dispensed in triplicate inside an anaerobic hood into serum bottles containing 1150 μg (4.8 μmoles) of each ferrite as prepared in Example 12. To each bottle was then added 0.10 mL of 4 mM $FeSO_4.7H_2O$ stock solution to give final concentrations of 10 $\mu M$ of iron. The bottles were sealed with butyl rubber stoppers and autoclaved. Each triplicate set of ferrites was inoculated with 0.2 ml early log phase (24 hr.-old culture) of the bacterial culture as described in Example 1 and incubated at $24°\pm1°$ C. for three days. Total gas and $CO_2$ production were measured. The bottles were then opened inside the anaerobic hood and pH and growth yield via turbidity (O.D.) were determined. The culture samples were then each filtered through a 0.22 $\mu m$ Millex filter to remove the bacteria and the supernate was acidified with 0.1 ml Ultrex $HNO_3$. Iron(II), iron-(III), in solution and organic acids in the supernate were analyzed. The results are shown in Tables V and VI below.

TABLE V

| | | Growth yield of Clostridium sp. in the presence of ferrites | | | | | |
|---|---|---|---|---|---|---|---|
| | | Growth | Total Gas | | Organic Acids* | | |
| Ferrite | pH | (Optical Density) | Produced (ml) | $CO_2$ ($\mu moles$) | Acetic ($\mu moles$) | Butyric ($\mu moles$) | Total ($\mu moles$) |
| None (control) | 3.00 ± 0.01 | 0.69 | 24.5 ± 0.0 | 856 ± 0 | 178 ± 0 | 321 ± 2 | 529 ± 16 |
| $CoFe_2O_4$ | 3.10 ± 0.02 | 0.68 | 30.6 ± 0.0 | 996 ± 0 | 215 ± 2 | 359 ± 4 | 604 ± 7 |
| $CuFe_2O_4$ | 3.06 ± 0.02 | 0.73 | 25.5 ± 3.6 | 788 ± 56 | 182 ± 23 | 301 ± 29 | 508 ± 66 |
| $MnFe_2O_4$ | 3.07 ± 0.01 | 0.68 | 27.2 ± 0.6 | 954 ± 10 | 208 ± 5 | 342 ± 4 | 584 ± 14 |
| $NiFe_2O_4$ | 3.04 ± 0.00 | 0.68 | 22.4 ± 0.0 | 800 ± 0 | 177 ± 9 | 297 ± 9 | 505 ± 13 |
| $ZnFe_2O_4$ | 3.02 ± 0.00 | 0.69 | 28.6 ± 0.0 | 936 ± 11 | 181 ± 1 | 318 ± 5 | 522 ± 11 |

*Includes minor amounts of propionic and lactic acids. Uninoculated control medium pH 6.82 ± 0.01.

Example 14

Dissolution in Uninoculated Growth Medium

In order to determine any dissolution of the ferrites by sterile bacterial growth medium, the procedure of Example 13 was followed except that the samples were not inoculated after autoclaving. This treatment determined the solubility of the ferrite in the uninoculated growth medium which served as the control. The results are shown in Table VI below.

TABLE VI

| | Dissolution of Ferrites by Clostridium sp. | | | | | |
|---|---|---|---|---|---|---|
| | Uninoculated Control (pH 6.8) | | Organic Acid Metabolites Medium (pH 3.2) | | Inoculated (pH 3.1) | |
| Ferrite | $Fe^{2+}$ | $M^{2+}$ | $Fe^{2+}$ | $M^{2+}$ | $Fe^{2+}$ | $M^{2+}$ |
| | | | $\mu moles$ in solution | | | |
| $CoFe_2O_4$ | 0.11 ± 0.02 | 0.76 ± 0.01 | 3.99 ± 0.34 | 3.50 ± 0.23 | 3.44 ± 0.35 | 1.66 ± 0.27 |
| $CuFe_2O_4$ | 0.55 ± 0.03 | <0.03 | 0.62 ± 0.04 | 0.54 ± 0.02 | 3.64 ± 0.36 | <0.03 |
| $MnFe_2O_4$ | <0.03 | 0.38 ± 0.01 | 0.08 ± 0.02 | 0.45 ± 0.00 | 2.26 ± 0.09 | 1.72 ± 0.04 |
| $ZnFe_2O_4$ | 0.13 ± 0.01 | 0.80 ± 0.04 | 0.05 ± 0.00 | 1.28 ± 0.09 | 0.36 ± 0.03 | 1.48 ± 0.03 |

Example 15

Indirect Microbial Dissolution of Ferrites By Organic Acid Metabolites Medium

To determine the extent of dissolution of the ferrites by the organic acid metabolites produced by the bacteria, a synthetic medium was prepared and it consisted of 4.5 mM acetic acid and 8.0 mM butyric acid (pH 3.2) in a mineral salts solution containing $MgSO_4.7H_2O$, 0.2 g; $CaCl_2.2H_2O$, 0.5 g; and $NH_4Cl$, 0.15 g per liter. The metabolic acids in the medium were added in the same proportions as found in a three-day-old inoculated culture of Clostridium sp. containing no ferrites. The ferrite samples as prepared in Example 12 in an amount of 1150 $\mu g$ in 60 mL of synthetic medium were incubated at $24°\pm1°$ C. for three days in a $N_2$ atmosphere and then filtered through a 0.22 $\mu m$ Millex filter, acidified with Ultrex $HNO_3$, and analyzed for ferric iron and metals. The results are shown in Table VI above.

Example 16

Dissolution of Copper Ferrite by Extracellular Components. Detailed studies were carried out with copper ferrite to determine if extracellular components produced by the bacterium caused dissolution of the ferrite. We compared the effects of filtered-cell-free spent medium containing extracellular enzymes and organic acid metabolites, and autoclaved filtered cell-free spent medium in which the enzymes were inactivated. For this purpose, Clostridium sp. was grown in culture medium without ferrite for 72 hrs. The culture medium was filtered through a 0.22 $\mu m$ Durapore filter (Millipore Co.) using a 1.5 L high pressure filtration device under anaerobic conditions. Forty mL of filtered-cell-free spent medium was added to 60 mL serum bottles containing 4.8 $\mu mole$ copper ferrite. This treatment determined enzymatic as well as non-enzymatic dissolution of copper ferrite. Another 40 mL of the filtered-cell-free spent medium was transferred to a serum bottle, fitted with a butyl rubber stopper, sealed with an aluminum cap and then autoclaved. After cooling, the medium was refiltered to remove any denatured material, and added, as before, to 60 mL serum bottles containing copper ferrite. This treatment determined the non-enzymatic dissolution of copper ferrite. The samples were incubated for 48 hrs and filtered through a 0.22 $\mu m$ Millex filter, acidified with Ultrex $HNO_3$, and analyzed for copper, ferrous and ferric iron. Controls without copper ferrite were included in the experiment. The results are shown in FIG. 4.

Figure 4:
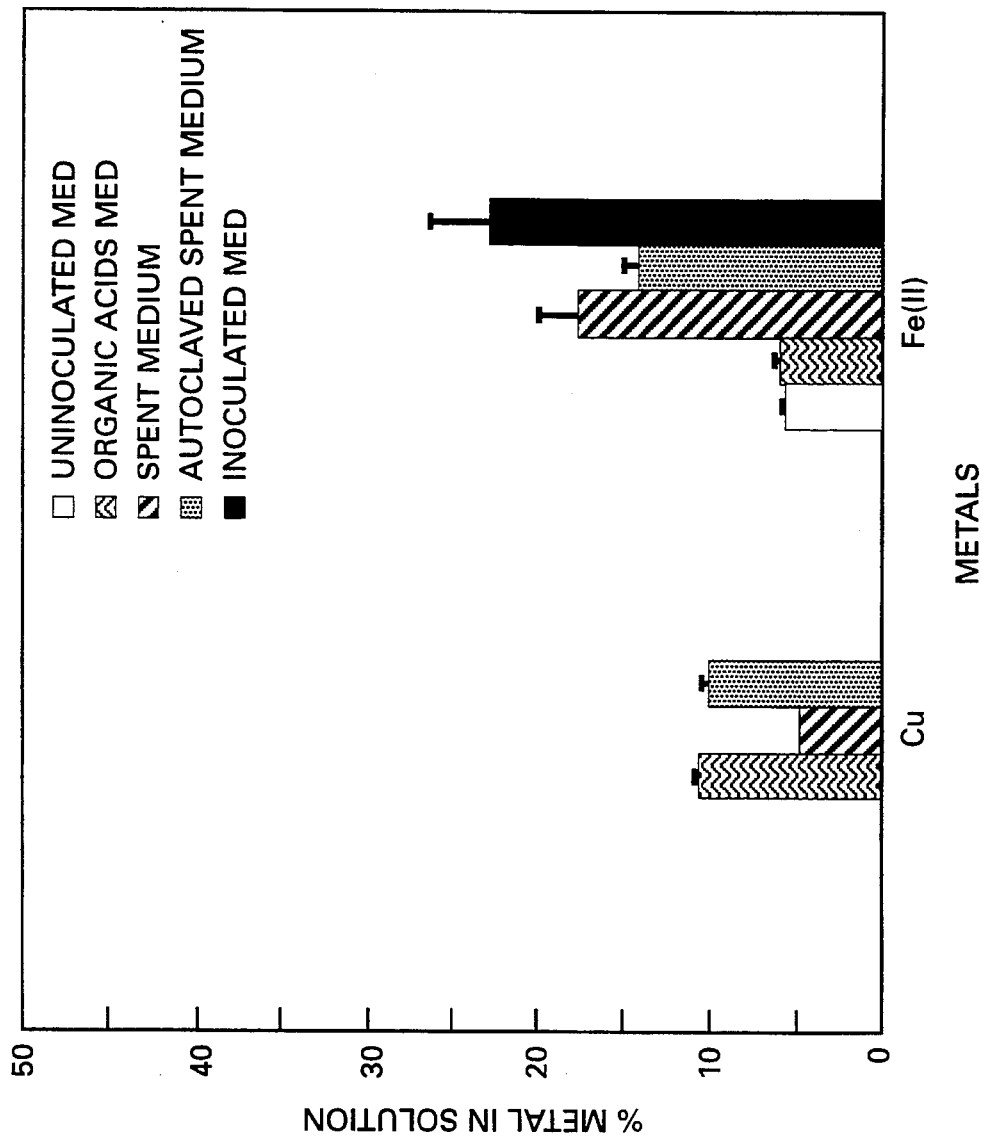
FIG. 4 is a graph comparing the dissolution of ferrite coprecipitates of copper under various conditions.

The bar graph in FIG. 4 shows the dissolution pattern of copper ferrite in (i) uninoculated medium, pH 6.8 (control) (unshaded bar), (ii) organic acid metabolites in the medium, pH 3.2 (chemical dissolution) (lightly shaded bar), (iii) cell-free spent medium, pH 3.1 (diagonally lined bar), (iv) autoclaved cell-free spent medium, pH 3.1 (nonenzymatic dissolution) (herring-bone bar)

and (v) medium inoculated with Clostridium sp., pH 3.1 (enzymatic and nonenzymatic dissolution) (darkly shaded bar).

Growth Characteristic of Bacteria. There were no obvious differences in the growth yield (optical density) of bacteria incubated with various ferrites for 3 days (Table V). However, there were differences in the total amounts of $CO_2$ and organic acid metabolites produced. Cobalt and manganese ferrites resulted in production of increased total gas, $CO_2$, and organic acid metabolites compared to samples with no ferrite. In the presence of zinc ferrite, an increase in total gas and $CO_2$ but not in organic acids, was observed. Acetic and butyric acids were the major organic acid metabolites found in all treatments. The ratio of acetic to butyric acids in samples with and without the ferrite ranged from 1:1.6 to 1:1.8. In the presence of manganese ferrite, the ratio was the lowest while in the presence of zinc ferrite, it was the highest. Minor amounts of lactic and propionic acids were also found in the culture medium. The final pH of the medium was acidic (pH 3.0) due to the presence of the organic acid metabolites.

Mechanisms of Dissolution of Ferrites. Table VI shows the dissolution of ferrites in uninoculated (control) medium, organic acid metabolites medium, and in medium inoculated with Clostridium sp. Cobalt ferrite was slightly soluble in the uninoculated (control) medium but readily soluble in the organic acid metabolites medium. About 45% of the iron (3.99 μmoles) and 72% of the cobalt (3.50 μmoles) were solubilized by the organic acid metabolites medium, suggesting that the dissolution of cobalt ferrite was due to indirect action. However, in the inoculated medium, 39% of the iron (3.44 μmoles) but only 34% of the cobalt (1.66 μmoles) was detected in solution.

Manganese from manganese ferrite was slightly soluble (9%) in the uninoculated medium but no iron was detected. The organic acid metabolites medium had little effect on the solubility of iron and manganese. However, a large increase in iron (23%) and manganese (42%) in solution was noted in the inoculated sample. Dissolution of iron from manganese ferrite was caused by bacterial reduction of iron with concurrent dissolution of manganese(II) by organic acid metabolites.

About 1.5% iron and 17% zinc was detected in solution in the uninoculated medium containing zinc ferrite. However, in the organic acid metabolites medium, there was a slight decrease in soluble iron (<1%) and a significant increase in soluble zinc (28%). In the inoculated sample, the concentration of iron increased to 4.1%, while there was only a slight increase in zinc concentration (32%) in solution compared to the organic acid metabolites medium. Dissolution of zinc ferrite was primarily due to the action of organic acid metabolites.

About 6% of Fe and no Cu (below detection limit) from copper ferrite was solubilized by the uninoculated control medium. In the organic acid metabolites medium, 11% of Cu and 7% of iron was solubilized. Cell-free spent medium that contained organic acid metabolites and extracellular enzymes showed 5% of Cu and 18% of Fe in solution. In the autoclaved cell-free spent medium, about 10% of Cu and 14% of Fe were solubilized from the ferrite. The amount of Cu solubilized by the autoclaved cell-free spent medium was comparable to organic acid metabolites medium indicating that $\approx 10\%$ of Cu from the ferrite was solubilized by the metabolic acids. In addition to chemical dissolution of Fe by the organic acid metabolites medium, heat-labile components present in the cell-free spent medium appear to be involved in the dissolution of Fe from the copper ferrite. In the inoculated samples, however, a substantial increase in the concentration of soluble Fe was observed while Cu concentration in solution was below the detection limit (<0.1%). The dissolution of iron from copper ferrite was due to bacterial reduction of ferric iron. The lower amount of Cu in the cell-free spent medium and in the inoculated medium was due to binding of Cu by extracellular components and by bacterial biomass, respectively.

Nickel ferrite showed no detectable dissolution in any treatments.

Example 7

Bioaccumulation of Co, Cu, Mn, and Zn. The extent of biosorption of Co, Cu, Mn, and Zn released from the ferrites by bacterial action was measured. Stock solutions of $CoCl_2.6H_2O$, 2.856 g; $CuCl_2.2H_2O$, 2.044 g; $MnCl_2.4H_2O$, 2.374 g; and $ZnCl_2.4H_2O$, 1.636 g in 1 L of deionized water were prepared to give a final concentration of 12.0 mM of metal. The pH of the solutions were adjusted to 3.2 with HCl and then pre-reduced. One milliliter of each of these pre-reduced stock solutions was added separately to 100 ml of a 48-hr old culture of Clostridium sp. Triplicate samples were incubated for 8 hr. At 2, 4, and 8 hr, 4 ml of the culture was withdrawn for measurements of turbidity and pH. The samples were filtered through a 0.22 μm Millex filter, acidified with Ultrex $HNO_3$, and the metals in solution were measured. Control samples without metals were included in this experiment. The results are shown in Table VII.

TABLE VII

| Biosorption of Metal Ions by Clostridium sp. | | | | |
|---|---|---|---|---|
| | Biosorption of Metal (%) | | | |
| Hour | Co | Cu | Mn | Zn |
| 2 | 3 ± 0 | 28 ± 0 | <1 | <1 |
| 4 | <1 | 29 ± 1 | 2 ± 0 | <1 |
| 8 | 2 ± 0 | 31 ± 0 | <1 | <1 |

Table VII shows the biosorption of Co, Cu, Mn, and Zn from solution by a growing culture of Clostridium sp. About 2% of Co and 31% of Cu which were added to the culture were removed from solution after 8 hrs of incubation. There was little change in the concentration of Mn and Zn.

Example 18

Dialysis experiments. To determine whether the stoichiometry of dissolution of iron and metal in normal and inverse spinels differed, as a result of bacterial activity and also to facilitate recovery of the residual ferrite, dialysis bag experiments were performed. For this purpose, a dialysis bag (Spectrapor, MWCO 12,000, Thomas Scientific Co.) containing 4.8 μmoles of $ZnFe_2O_4$ or $CuFe_2O_4$ was placed in a serum bottle containing 40 ml of medium. The open end of the bag was placed around the mouth of a serum bottle, and the bottle was closed with a butyl rubber stopper in such a way to allow addition of inoculum directly into the bag through the stopper. The bottles with the dialysis bags containing the ferrite were autoclaved. A 0.2 ml of a 24-hr old culture of Clostridium sp. was inoculated directly into the dialysis bag, and the samples incubated for 72 hr at 24°±1° C. After incubation, the dialysis bag was removed, its contents digested with $HNO_3$, and analyzed for metals. Similarly, the medium surrounding the bag was digested an analyzed. An uninoculated sample with the ferrite in the dialysis bag and the medium outside of the bag was used as control. All samples were measured in quadruplicate. The results are shown in Table VIII.

TABLE VIII

| | | Dissolution pattern of normal and inverse ferrites | | | | | |
|---|---|---|---|---|---|---|---|
| | | Outside dialysis bag (in solution) | | Ratio | Inside dialysis bag (insoluble form)* | | Ratio |
| Ferrite | Treatment | $Fe^{2+}$ | $M^{2+**}$ | $Fe^{2+}/M^{2+}$ | $Fe^{2+}$ | $M^{2+}$ | $Fe^{2+}/M^{2+}$ |
| $ZnFe_2O_4$ (normal) | Uninoculated Control | <0.10 | 0.35 ± 0.01 | — | 8.97 ± 0.25 | 5.08 ± 0.15 | 1.8 |
| | Incoulated | 2.04 ± 0.14 | 2.16 ± 0.09 | 0.9 | 7.07 ± 0.13 | 3.41 ± 0.16 | 2.1 |
| $CuFe_2O_4$ (inverse) | Uninoculated | <0.10 | 0.17 ± 0.00 | — | 10.0 ± 0.1 | 4.69 ± 0.03 | 2.1 |
| | Inoculated | 4.83 ± 0.10 | −0.05 | — | 6.89 ± 0.14 | 5.79 ± 0.20 | 1.1 |

*Insoluble form refers to unreacted minerals and/or reprecipitated metal ion.
**$M^{2+}$ - Metal.

Dissolution pattern of normal and inverse ferrites. In Table VIII, the dissolution pattern is presented for normal (zinc) and inverse (copper) spinel placed inside the dialysis bags with the bacteria. The tetrahedral and the octahedral structures of the normal spinel, zinc ferrite, are composed of Zn and Fe, respectively. In the uninoculated control sample, a small amount of Zn and no iron from zinc ferrite was detected in solution. However, in the inoculated sample, significant amounts of iron and zinc were found in solution outside the dialysis bag. The amount of zinc in solution was approximately the same as iron (a ratio of 0.9:1) indicating that iron and zinc were solubilized simultaneously by bacterial action. Analysis of the inside contents of the dialysis bag containing residual ferrite showed a molar ratio of iron to zinc 2.1:1, a slight enrichment of Fe compared to the starting material (Table (VIII).

In copper ferrite, the tetrahedral structure is composed only of Fe, and the octahedral structure is composed of a mixture of Cu and Fe in a 1:1 ratio. In the uninoculated sample, a small amount of soluble Cu but no Fe was detected outside the dialysis bag. However, in the inoculated sample, a significant amount of ferrous iron but no copper was found in solution outside the bag. Analysis of the inside contents of dialysis bag containing residual ferrite showed an enrichment of copper relative to iron. The ratio of Fe to Cu was 1.1:1 instead of 2:1, suggesting the possibility that the Fe in the tetrahedral structure was solubilized by the bacteria by enzymatic reduction of ferric iron, leaving the octahedral Fe and Cu intact.

Dissolution of the ferrites is brought about by enzymatic reduction of iron (direct action) and by organic acid metabolites (indirect action). We found differences in the extent of dissolution of the ferrites tested.

There was no clear-cut relationship between the type of ferrite (normal vs. inverse spinels) and the mechanism of dissolution. For example, cobalt ferrite (inverse spinel) was solubilized by indirect action, copper (inverse spinel) and manganese (normal spinel) ferrites by direct action, while zinc ferrite (normal spinel) was solubilized by both direct and indirect actions. In general, dissolution of iron from the normal (octahedral coordination) and inverse (tetrahedral coordination) spinels was due to direct action of the bacteria.

These results show that metal ions in a liquid can be precipitated and concentrated with ferrites and the ferrites can be solubilized by direct or indirect actions of bacteria under anaerobic conditions.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A method for remobilizing a coprecipitated metal from an iron oxide/metal coprecipitate comprising contacting the coprecipitate with a biologically pure bacterial culture of Clostridium sp. ATCC 53464 under conditions sufficient to sustain the viability of the bacteria and in a medium which satisfies the nutritional requirements of the bacteria so that the coprecipitated metal is solubilized or incorporated into biomass by said bacterial culture.

2. The method of claim 1 wherein the contacting is under essentially anaerobic conditions.

3. The method of claim 1 wherein the contacting is at a temperature of from about 15° C. to about 37° C., at an initial pH of from about 4 to about 8, for a time of from about 1 second to about 48 hours, and at a pressure of from about 0 to about 20 psig.

4. The method of claim 1 wherein the coprecipitated metal is solubilized by contact with the bacterial culture.

5. The method of claim 1 wherein the coprecipitated metal is incorporated into biomass by the bacterial culture.

6. The method of claim 1 which further comprises first concentrating metal ions from a liquid containing said metal ions by treating the liquid with an iron oxide coprecipitating agent to form an iron oxide/metal coprecipitate containing the metal ions and removing the coprecipitate from the liquid.

7. The method of claim 6 wherein the treating is at temperature of from about 0° C. to about 110° C. and at a pH of about 7.5 to 14.

8. The method of claim 6 wherein the liquid is aqueous.

9. The method of claim 8 wherein the aqueous liquid is a wastestream.

10. The method of claim 9 wherein the wastestream is selected from the group consisting of mining effluent, fossil and nuclear fuel cycle wastes, geothermal waste and electroplating and metal finishing wastes.

11. The method of claim 1 wherein the metal is selected from the group consisting of members of groups IA, IIA, IIIA, IVA, VA, VIA, IB, IIB, IIIB, IVB, VB, VIB, VIIB, VIII, Lanthanides and Actinides of the Periodic Table of the Elements and transuranic metals.

12. The method of claim 11 wherein the metal is selected from the group consisting of arsenic, cadmium, cobalt, chromium, copper, nickel, lead, uranium, plutonium, zinc, gold, silver, platinum and palladium.

13. The method of claim 6 wherein the coprecipitating agent is selected from the group consisting of magnetite, hematite, limonite, goethite and ferrite.

14. The method of claim 13 wherein the coprecipitating agent is selected from the group consisting of goethite and ferrite.

15. The method of claim 1 wherein the contacting is in a batch process.

16. The method of claim 1 wherein the contacting is in a continuous process.

17. A process for removing metal ions from an aqueous liquid comprising:

concentrating the metal ions by treating the aqueous liquid with a coprecipitating agent selected from the group consisting of magnetite, hematite, limonite, goethite and ferrite at a temperature of from about 0° C. to about 110° C., at a pH of from about 7.5 to 14, with the amount of the coprecipitating agent being in excess of the amount of metal ions, to form a coprecipitate;

removing the coprecipitate of said coprecipitating agent and said metal ions from the aqueous liquid;

contacting the coprecipitate with a pure bacterial culture of Clostridium sp. ATCC 53464 under essentially anaerobic conditions at a temperature of from about 15° C. to about 37° C., at pH of from about 4 to 8 and a time of from about one second to about 48 hours in the presence of a nutrient medium which satisfies nutritional requirements of the Clostridium sp. to solubilize the metal ions from the coprecipitate; and removing the metal ions from the medium.

* * * * *